US012514677B2

(12) United States Patent
Siccardi et al.

(10) Patent No.: US 12,514,677 B2
(45) Date of Patent: Jan. 6, 2026

(54) SUTURE WITH A PLURALITY OF COLOR MARKS

(71) Applicant: Medacta International SA, Castel San Pietro (CH)

(72) Inventors: Francesco Siccardi, Morcote (CH); Ernst Kehrli, Sins (CH); Sascha Berberich, Tuttlingen (DE); Philippe Gédet, Ipsach (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 311 days.

(21) Appl. No.: 17/760,148

(22) PCT Filed: Feb. 3, 2021

(86) PCT No.: PCT/EP2021/052554

§ 371 (c)(1),
(2) Date: Aug. 4, 2022

(87) PCT Pub. No.: WO2021/160491

PCT Pub. Date: Aug. 19, 2021

(65) Prior Publication Data

US 2023/0079284 A1 Mar. 16, 2023

(30) Foreign Application Priority Data

Feb. 13, 2020 (IT) ........................ 102020000002938

(51) Int. Cl.
*A61B 90/92* (2016.01)
*A61B 17/06* (2006.01)
*A61B 17/00* (2006.01)

(52) U.S. Cl.
CPC ........ *A61B 90/92* (2016.02); *A61B 17/06166* (2013.01); *A61B 2017/00526* (2013.01); *A61B 2017/0619* (2013.01)

(58) Field of Classification Search
CPC .......................... A61B 90/92; A61B 17/06166
See application file for complete search history.

(56) References Cited

U.S. PATENT DOCUMENTS

2008/0051834 A1 2/2008 Mazzocca et al.
2015/0045831 A1 2/2015 Allen
(Continued)

FOREIGN PATENT DOCUMENTS

EP 0554653 A2 8/1993
EP 2251045 A2 11/2010
(Continued)

OTHER PUBLICATIONS

Japanese Office Action issued Oct. 8, 2024 for Japanese Patent Application No. 2022-548857.

*Primary Examiner* — Erin Mcgrath
(74) *Attorney, Agent, or Firm* — Husch Blackwell LLP

(57) ABSTRACT

A suture includes an outer sheath with color marks and a background visually distinguishable from the color marks. Each color mark has exposed portions of at least two colored yarns of first and second different colors. The background includes exposed portions of background yarns of a background color. The background yarns and the colored yarns are braided to each other. The first and second colors are different from the background color. The color marks are arranged in at least one row along a longitudinal direction of the suture. Each color mark is longitudinally shifted with respect to a subsequent color mark in a same row by a first shift, and the exposed portions of the colored yarns of each color mark are substantially parallel to each other and arranged in a sequence along the longitudinal direction of the suture.

13 Claims, 2 Drawing Sheets

(56) References Cited

U.S. PATENT DOCUMENTS

| | | | |
|---|---|---|---|
| 2015/0173753 | A1 | 6/2015 | Spivey et al. |
| 2017/0156727 | A1* | 6/2017 | Wilson-Wirth ....... A61L 17/105 |

FOREIGN PATENT DOCUMENTS

| | | | |
|---|---|---|---|
| GB | 2468307 | A | 9/2010 |
| JP | 5-253232 | A | 10/1993 |
| JP | 2010-255175 | A | 11/2010 |

* cited by examiner

SUTURE WITH A PLURALITY OF COLOR MARKS

CROSS REFERENCES

This application is a U.S. National Phase Application of International Application No. PCT/EP2021/052554 filed on Feb. 3, 2021, which in turn claims priority to Italian Application No. 102020000002938 filed on Feb. 13, 2020, the disclosures of which are incorporated herein by reference in their entireties.

TECHNICAL FIELD

The present invention relates to a suture of the type used to connect tissue portions, in an effort to facilitate proper healing.

BACKGROUND ART

Sutures are tied around the tissue edges and knotted so as to ensure strong anchoring to the tissue.

During suturing it may be necessary for a medical professional to distinguish between the ends of similar sutures in order to correctly knot the suture, which becomes more difficult when both ends of the suture have an identical visual appearance. A correct knotting of sutures is essential because, if knotted improperly, the suture could damage tissue or not adequately secure the tissue.

Suturing procedures can be particularly challenging especially in minimally invasive surgical procedures, such as endoscopic or arthroscopic surgical procedures, the advent of which has put additional pressure on surgeons to correctly identify sutures and their respective ends for proper tying of knots in confined spaces.

Problems encountered by a surgeon in minimal invasive procedures include reduced visibility and field of vision, as well as potential orientation difficulties when performing the required manipulations at the surgical site. For example, when the suture is applied in an arthroscopic procedure, only a small portion of the suture may be visible, and at least some tissue parts through which the suture passes may not be visible at all when the suture is knotted and/or tensioned. Or else, when a suture is looped through the tissue and both ends extend therefrom, it can be difficult to determine which one of the ends of the sutures should be tensioned if they have a same appearance. Also, when a plurality of sutures having a same appearance are used, it can be difficult to identify which one should be tensioned, and in which direction.

As a specific example, it can be difficult for a surgeon to determine the suture orientation or the direction of motion for example when, during a repairing procedure of the rotator cuff, reattachment of the rotator cuff tendon back to the humerus is required. This repair procedure consists of a tied medial row with one or more knotless lateral fixation anchors. One of the risks related to this procedure is the mix-up or confusion of the strands when configuring and knotting them with the anchors according to the surgical technique, especially when arthroscopically performed.

US2015173753A1 discloses a surgical device, comprising a suture configured to engage tissue of a patient, the suture including a first plurality of threads of a first color and a second plurality of threads of a second color, the first plurality of threads being braided with the second plurality of threads such that directional arrows formed only from the second plurality of threads are present on an external surface of the suture and are visually discernable by a human user of the suture, all of the directional arrows pointing in a same direction.

The second threads, forming the arrows, have a different contrasting color with respect to the first threads, forming the background. Different colors are provided only to discern the arrows with respect to the background.

The Applicant observes that the provision of a geometric pattern such as arrows involves structural constraints on the threads constituting the suture, especially for the threads forming the pattern. Indeed, the pattern might be less visible and in particular the orientation of the arrow elements might be less recognizable by a user for example if the threads are too thin, or else if the threads used are too thick, in which case the shape of the arrow elements might depart from that of a well-defined arrow, with a clearly distinguishable arrowhead.

Another conventional way to aid a surgeon in distinguishing an incoming end from an outgoing end of a suture, is to use a "half and half" suture, in which one half or end has a different appearance (for example, pattern or color) with respect to a second half or end.

For example, EP2251045A2 discloses a suture comprising an elongate woven braid of fibers comprising one or more first ends comprising ultra-high molecular weight polyethylene; at least one second end comprising a colorable material wherein the second end is a single continuous color; and at least one third end comprising a dyeable material wherein at least a portion of the third end is dyed a continuous color. The document further discloses that such portion can be for example half of the end, thereby providing two distinguishable halves of the suture.

Also US2015045831A1 provides a suture with different possible "half and half" configurations. The document discloses a surgical braid comprising a plurality of strands arranged in a braid, the braid comprising at least first and second sections; and the plurality of strands comprising at least one strand having a first color, the at least one strand having a first color being braided into the first section in a first pattern, the at least one strand having a first color being braided into the second section in a second pattern.

The document also discloses a surgical braid comprising a plurality of strands arranged in a braid; and the plurality of strands comprising at least first and second strands having a color, the first strand being braided in a pattern along at least a portion of the braid, the second strand being braided in a different pattern along at least a portion of the braid.

Moreover, the document discloses a surgical braid comprising a plurality of fibers arranged in a tubular braid, the tubular braid comprising an outer wall and at least first and second sections, the first section having a first core and the second section having a second core; and the plurality of fibers comprising at least one fiber having a first color, the at least one fiber having a first color being braided into the outer wall of the first section and forming the second core in the second section.

The Applicant observes that although the "half and half" configuration provided in these documents allows the medical professional to distinguish the two different ends of a same suture, it offers little help in determining a running direction of the suture (for example, incoming or outgoing end) in highly complex situations, for example when multiple sutures are simultaneously employed or for example when a running direction of a suture portion already looped through the tissue has to be determined. In these cases, there is no clear distinction between the various incoming and outgoing ends or portions of the various sutures.

SUMMARY

The problem at the basis of the invention is therefore to provide an improved suture that overcomes the problems found in the prior art, the suture having marks on its external surface that are easily visible and help the medical professional to distinguish the ends of the suture and to identify the travel direction of the suture during the suturing procedure, thereby allowing a better and more reliable knotting of the suture.

According to a first aspect, the invention relates to a suture having an outer sheath comprising a plurality of color marks and a background visually distinguishable from the color marks, wherein each color mark comprises exposed portions of at least two colored yarns of respective first and second colors, and wherein said background comprises exposed portions of background yarns of a background color, said background yarns and said at least two colored yarns being braided to each other, said first and second colors being different from said background color and said first color being different from said second color.

Said plurality of color marks are arranged in at least one row along a longitudinal direction of the suture, each color mark being longitudinally shifted with respect to a subsequent color mark in a same row by a first shift. The exposed portions of the at least two colored yarns of each color mark are substantially parallel to each other and arranged in a sequence along the longitudinal direction of the suture.

The color marks, provided on the external surface of the suture of the invention, constitute an effective directional indication since the exposed portions of the at least two colored yarns of respective first and second colors in combination with the background provide for a visual asymmetric aspect of the suture. Such color marks can be advantageously used to determine the two ends and the direction of application of the suture, thereby providing an effective aid for the physician/surgeon when applying the suture.

The order of the colored exposed portions forming the color marks is different when observed from one end or the other of the suture. Therefore, once the medical professional has determined a reference running direction of the suture, that direction is related to a fixed "color code" determined by the specific order, along that running direction, of the colored exposed portions forming each color mark.

A suitable selection of different first and second colors of the first and second yarns, as well as a suitable background color for the background yarns, allows to properly highlight the color marks and their "color code" with respect to the background, so that the color marks can be easily detected and interpreted by the medical professional during the suturing procedure.

The Applicant has perceived that the provision of a directional indication based on a "color code" is more easily visible and interpretable with respect to a simple geometric pattern, considering the typically limited dimensions of a suture and the possible geometric/structural constraints to be taken into account to choose a geometric pattern.

In addition, the Applicant notes that since the color marks are repeated in a regular pattern along the entire length of the suture, not only they allow the medical professional to distinguish between the different free ends of a suture, but remarkably aid in distinguishing the incoming/outgoing suture(s) even in very complex scenarios, for example when a plurality of sutures are involved, and also in distinguishing the incoming/outgoing direction of looped portions of the sutures.

Thanks to its improved running direction indication performed by the innovative color marks, the suture of the invention is especially suitable for use in minimal invasive procedures such as arthroscopic or endoscopic procedures in which, as outlined above, a high degree of complexity can be reached due to the high number of sutures involved and the narrow field of vision. The suture of the invention helps to reduce the risk of fatal suture tangling and allows to reduce the knotting time.

The present invention can have, in one or more of the aspects thereof, one or more of the preferred features described hereinafter, which can be combined with one another as desired depending on the application requirements.

Within the framework of the present description and in the following claims, all numerical values indicating amounts, parameters, percentages and so on are always to be intended as preceded by the term "about", if not otherwise stated. Moreover, all numerical value ranges include all possible combinations of the maximum and minimum numerical values and all possible intermediate ranges, besides those specifically indicated below.

In the present description and in the attached claims, the terms "radial", "circumferential", "inner", "outer" and similar terms are used with reference to cross-sections of the yarns or of the overall suture.

Preferably, the suture of the invention is fabricated using a suitably configured circular braiding machine, such as a maypole braiding machine.

Preferably, the suture is manufactured by a maypole braiding machine comprising bobbin carriers mounted onto horn gears, divided into two sets of bobbin carriers. The yarns to be braided are rewound on a bobbin, one free end of each yarn being collected by a hub positioned vertically above the revolving bobbin carriers.

The two sets of bobbin carriers of the tubular braiding machine rotate on a closed circular track, one set turning clockwise around the center of the machine, and the other set turning in counterclockwise direction. While revolving in opposite directions, the bobbin carriers are diverted to pass alternately inside and outside (under and over) one another. The clockwise and counterclockwise paths cause the two sets of yarns to intersect, thus producing a tubular braid. The tubular braids can be made coreless, or alternatively yarns can be braided around a core yarn.

The maypole braiding machine always has an even number of bobbin carriers, so that an equal numbers of bobbin carriers are provided for each of the two circular directions.

Based on the occupation of the bobbin carriers, namely the number of bobbin carriers that are actually carrying a yarn with respect to the total number of bobbin carriers of the machine, different braiding configurations can be obtained.

Preferably, the outer sheath of the suture has a two over/two under braiding configuration.

The two over/two under configuration provides that if one follows the path of a yarn, it can be recognized that it is alternately overlaying two yarns before being superimposed by the following two yarns.

Preferably, during manufacturing of the suture, the at least two colored yarns are placed on bobbin carriers belonging to a same set of bobbin carriers, for example they are all placed on clockwise bobbins or on counterclockwise bobbins. This implies that in the outer sheath of the final suture, the at least two colored yarns are all similarly oriented as outlined above.

Preferably, in each color mark said exposed portions of the at least two colored yarns are adjacent to one another along the longitudinal direction of the suture.

By providing adjacent exposed portions of the at least two colored yarns, the resulting color marks are more compact and better distinguishable with respect to the background.

This configuration is obtained when, during manufacturing of the suture, the at least two colored yarns are placed on adjacent bobbin carriers of a same set of clockwise/counterclockwise bobbin carriers, namely they are placed on bobbin carriers that are sequential along the corresponding clockwise/counterclockwise path along the horn gears of the maypole braiding machine.

Preferably, the remaining bobbin carriers of the same set of bobbin carriers carrying the at least two colored yarns, as well as the bobbin carriers belonging to the other set of bobbin carriers (e.g., the counterclockwise bobbins if the at least two colored yarns are placed on clockwise bobbins, or vice versa), are occupied by background yarns.

Preferably, said at least one row along the longitudinal direction of the suture comprises a plurality of rows circumferentially spaced from adjacent ones by at least one background row, said at least one background row comprising only exposed portions of background yarns.

This configuration allows the user's visual observation and recognition of the color marks from different angles with respect to the suture, for example when the suture is bent or twisted.

Preferably, said plurality of rows comprises at least two rows circumferentially spaced apart from adjacent ones.

Preferably, a number n of rows of said plurality of rows is calculated as follows:

$$n=1/X \tag{1}$$

with X being:

$$X=4/b \tag{2}$$

with b being equal to the total number of bobbin carriers of the braiding machine used to manufacture the suture.

More preferably, said at least two rows are circumferentially spaced from adjacent ones by a same circumferential angle α.

Preferably, said circumferential angle α is calculated as follows:

$$\alpha=X*360^\circ \tag{3}$$

For example, in a preferred embodiment in which the braiding machine comprises 16 bobbin carriers, X is equal to ¼ and said plurality of rows thus comprises four rows circumferentially spaced apart from adjacent ones by 90°.

In another exemplary embodiment in which the braiding machine comprises 12 bobbin carriers, X is equal to ⅓ and said plurality of rows thus comprises three rows circumferentially spaced apart from adjacent ones by 120°.

This configuration is sufficient for the color marks to be visible from substantially any angular position of an observer with respect to the suture.

Preferably, each color mark is longitudinally shifted with respect to a subsequent color mark in a same row of any row by said first shift.

In this way, a regular pattern is obtained on the outer surface of the suture along its length.

Preferably, any color mark of a first row is longitudinally shifted by a second shift with respect to a corresponding color mark in a second row circumferentially subsequent to the first row.

Preferably, all the color marks of the suture are ideally crossed by a number of ideal helixes all having a constant pitch.

In particular, said constant pitch of the ideal helixes is equal to the first shift.

This configuration provides a particularly homogeneous and regular distribution of the color marks on the outer surface of the suture.

Preferably, said first shift is defined by a number of subsequent and adjacent exposed portions of yarns along a longitudinal direction, wherein said number of subsequent and adjacent exposed portions of yarns is equal to half of the total number of braided yarns of the suture.

For example, when the suture consists of sixteen braided yarns, the first shift is equal to 8.

Preferably, said second shift is defined by a number of subsequent and adjacent exposed portions of yarns along a longitudinal direction, wherein said number of subsequent and adjacent exposed portions of yarns is constant and depends on the braiding configuration adopted.

In general, both the values of the first and the second shifts depend in particular on the setting of the maypole braiding machine, detailed above.

The second shift is preferably calculated according to the following formula:

$$S2=X*S1 \tag{4}$$

Wherein S1 is the first shift, and X is calculated according to the above formula (2).

For example, when the braiding machine comprises 16 bobbin carriers and the first shift S1 is equal to 8 (calculated as explained above), X is equal to ¼ and the second shift is equal to 2.

Preferably, an absolute value of the braiding angle of braided yarns of the outer sheath of the suture is comprised between 20° and 60°.

Preferably, each color mark comprises more than 2 exposed portions of colored yarns, wherein at least two colored yarns respectively have said first and second color, and wherein the remaining colored yarns have a respective color selected from said first color, said second color and at least one other color different from said first and second color.

Preferably, each color mark comprises less than 13 exposed portions of colored yarns, wherein at least two colored yarns respectively have said first and second color, and wherein the remaining colored yarns have a respective color selected from said first color, said second color and at least one other color different from said first and second color.

Preferably, each color mark comprises more than 3 exposed portions of colored yarns, wherein at least two colored yarns respectively have said first and second color, and wherein the remaining colored yarns have a respective color selected from said first color, said second color and at least one other color different from said first and second color.

Preferably, each color mark comprises less than 12 exposed portions of colored yarns, wherein at least two colored yarns respectively have said first and second color, and wherein the remaining colored yarns have a respective color selected from said first color, said second color and at least one other color different from said first and second color.

Preferably, each color mark comprises more than 4 exposed portions of colored yarns, wherein at least two colored yarns respectively have said first and second color, and wherein the remaining colored yarns have a respective color selected from said first color, said second color and at least one other color different from said first and second color.

Preferably, each color mark comprises less than 11 exposed portions of colored yarns, wherein at least two colored yarns respectively have said first and second color, and wherein the remaining colored yarns have a respective color selected from said first color, said second color and at least one other color different from said first and second color.

Preferably, each color mark comprises more than 5 exposed portions of colored yarns, wherein at least two colored yarns respectively have said first and second color, and wherein the remaining colored yarns have a respective color selected from said first color, said second color and at least one other color different from said first and second color.

Preferably, each color mark comprises less than 10 exposed portions of colored yarns, wherein at least two colored yarns respectively have said first and second color, and wherein the remaining colored yarns have a respective color selected from said first color, said second color and at least one other color different from said first and second color.

Preferably, each color mark comprises more than 6 exposed portions of colored yarns, wherein at least two colored yarns respectively have said first and second color, and wherein the remaining colored yarns have a respective color selected from said first color, said second color and at least one other color different from said first and second color.

Preferably, each color mark comprises less than 9 exposed portions of colored yarns, wherein at least two colored yarns respectively have said first and second color, and wherein the remaining colored yarns have a respective color selected from said first color, said second color and at least one other color different from said first and second color.

Preferably, each color mark comprises more than 7 exposed portions of colored yarns, wherein at least two colored yarns respectively have said first and second color, and wherein the remaining colored yarns have a respective color selected from said first color, said second color and at least one other color different from said first and second color.

Preferably, each color mark comprises less than 8 exposed portions of colored yarns, wherein at least two colored yarns respectively have said first and second color, and wherein the remaining colored yarns have a respective color selected from said first color, said second color and at least one other color different from said first and second color.

The above lower numbers of exposed portions of colored yarns can be combined with any of the above upper numbers of exposed portions of colored yarns as desired.

Therefore, according to the invention each color mark can comprise e.g. from 2 to 13, or from 3 to 12, or from 4 to 11, or from 5 to 10, or from 6 to 9, or from 7 to 8, exposed portions of colored yarns, wherein at least two colored yarns respectively have said first and second color, and wherein the remaining colored yarns have a respective color selected from said first color, said second color and at least one other color different from said first and second color.

This number of colored yarns having (at least two) different colors is sufficient to form color marks that can be easily detected and recognized by a user.

Preferably, each color mark comprises from 3 to 5 exposed portions of colored yarns, wherein at least two colored yarns respectively have said first and second color and wherein the remaining colored yarns have a respective color selected from said first color, said second color and at least one other color different from said first and second color.

In this way, the resulting color marks are even more easily distinguishable.

Preferably, each colored yarn is either of the first color or of the second color.

By using colored yarns of just two different colors, the resulting "color code" is particularly simple and easy to recognize and memorize for the user.

Preferably, in each color mark having more than two exposed portions of colored yarns, exposed portions of colored yarns of the same color are adjacent to each other. In this way, the color marks consist of two clearly distinguished regions of different colors.

Preferably, the raw material of all the yarns constituting the outer sheath of the suture is UHMWPE.

UHMWPE is a biocompatible non-absorbable material that is widely used in the biomedical field, particularly suitable for high strength appliances due to its excellent strength combined with a good flexibility when spinned into fibers. UHMWPE also shows a higher abrasion resistance when compared to other materials such as for example polyester and other favourable properties such as a high maximal tensile strength.

BRIEF DESCRIPTION OF THE DRAWINGS

A non-limiting embodiment of the present invention will now be described, by way of example, with reference to the accompanying drawings, in which.

DETAILED DESCRIPTION

Figure 1:
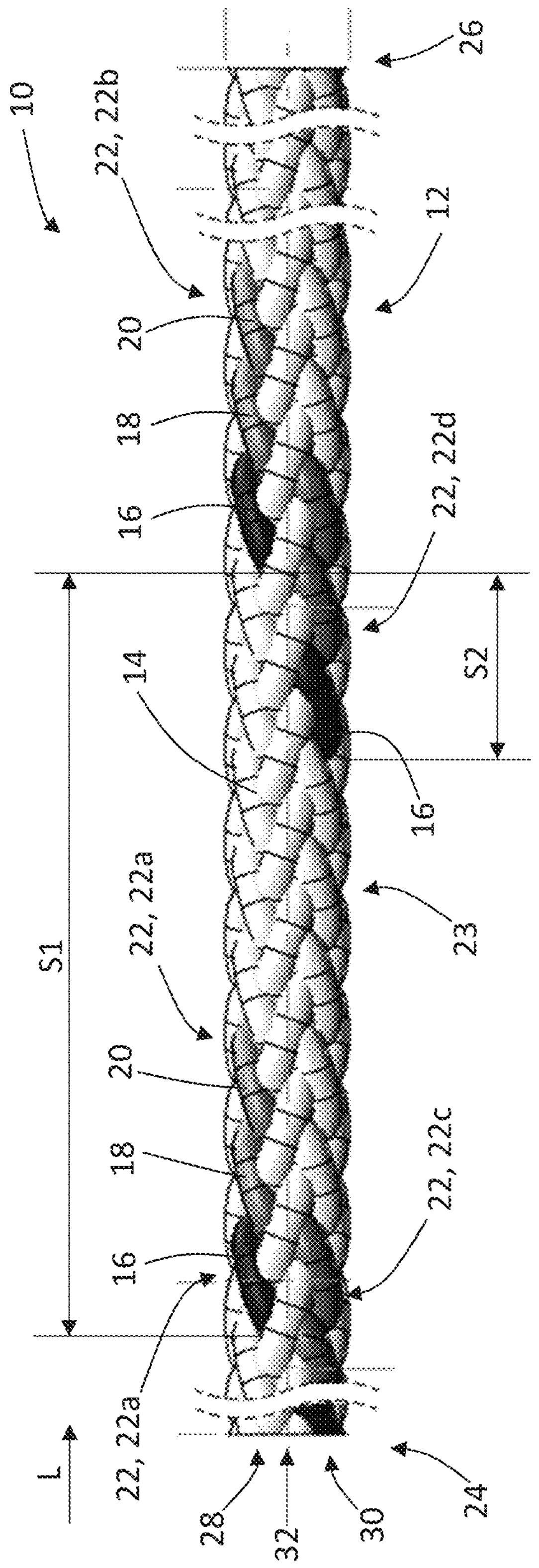
FIG. 1 is a schematic representation of a suture having color marks, according to an embodiment of the invention.

FIG. 1 schematically illustrates a suture 10 according to an embodiment of the invention. The suture 10 is in particular a suture thread, and comprises an outer sheath 12 formed by braiding a plurality of yarns. The outer sheath 12 comprises, on an outer surface thereof, a plurality of color marks 22*a*, 22*b*, 22*c* and 22*d* (also indicated with the general reference 22) that are visually distinguishable from a background 23.

The plurality of yarns of the suture 10 comprises background yarns 14 having a background color and thereby forming the background 23, and at least two colored yarns, comprising a first yarn 16 and a second yarn 18 of respective first and second colors that are different and contrasting from one another and with respect to the background color. In FIG. 1, the background color is represented by white, the first color by black and the second color by grey.

Indeed, the color marks 22 are formed of exposed portions of the colored yarns 16, 18, arranged in a sequence along the longitudinal direction L of the suture 10. The exposed portions of the first and second yarns 16, 18 of all color marks 22 run parallel to each other.

The color code identified by the sequence of the exposed portions of the first and second yarns 16, 18 of each color mark 22 is different if observed along a reference longitudinal direction (such as the longitudinal direction L indicated in FIG. 1, running from a first end 24 to a second end 26 of the suture 10) or from an opposite longitudinal direction (the direction from the second end 26 to the first end 24 of the suture 10). As already outlined, the color marks 22 provide an advantageous directional indication onto the outer sheath 12 of the suture 10, that can be advantageously used to aid the physician/surgeon to determine the running direction of the suture during surgery.

As will be explained in more detail with reference to FIG. 3-4 later described, in the configuration shown each color mark 22 can comprise further colored yarns up to a total of seven colored yarns.

For example the color marks 22 shown in FIG. 1 further comprise an exposed portion of a third yarn 20, having a third color, as illustrated in FIG. 1.

The third color of the third yarn 20 can be the same as the second color of the second yarn 18 (as in FIG. 1, again represented by grey), or it can be different.

The outer sheath 12 of the suture 10 preferably comprises a total of sixteen braided yarns, three of which being colored yarns (first, second and third yarns 16, 18, 20) and the remaining being background yarns 14.

The color marks 22 are repeated, all equal to each other, along the whole length of the suture 10 and in particular they are arranged in a plurality of rows 28, 30 running along the longitudinal direction L of the suture 10. In FIG. 1 four marks 22*a*, 22*b*, 22*c* and 22*d* are, distributed in two rows 28, 30.

Although in FIG. 1 only two rows 28, 30 of color marks 22 are visible, the outer sheath 12 of the suture 10 comprises four rows equally distributed along a circumference of the outer sheath 12, therefore circumferentially spaced apart from adjacent ones by 90°.

The rows 28, 30 and the two further rows (not visible) along the circumference of the outer sheath 12 are each separated from adjacent ones by at least one background row 32 comprising only exposed portions of background yarns 14.

As shown in FIG. 1, exposed portions of background yarns 14 of the at least one background row 32, positioned between two subsequent rows 28, 30, are parallel to each other but oriented, with respect to the longitudinal direction L, with an opposed angle with respect to the exposed portions of the first, second and third yarns 16, 18, 20, with respect to the longitudinal direction L.

In any row 28, 30, the color marks 22 are longitudinally shifted with respect to adjacent ones in a same row by a same first shift S1. In particular, each color mark 22 is longitudinally shifted by said first shift S1 with respect to a subsequent color mark in a same row 28, 30.

For example, the color mark 22*a* is longitudinally shifted by said shift S1 with respect to the subsequent color mark 22*b*, arranged along the same row 28, and the color mark 22*c* is longitudinally shifted by the same shift S1 with respect to the subsequent color mark 22*d*, arranged along the same row 30.

The first shift S1 is in particular defined by a number of subsequent and adjacent exposed portions of yarns along the longitudinal direction L. In other words, the first shift is determined by counting the adjacent exposed portions of yarns while moving from the beginning of a color mark 22 to the beginning of the following color mark 22 belonging to the same row 28, 30 (or, in an equivalent manner, between the end of a color mark 22 and the end of the following color mark 22).

The first shift S1 is in particular equal to half of the total number of braided yarns constituting the suture 10. For example, in the case of FIG. 1 in which the suture 10 consists of 16 braided yarns, the first shift for all the color marks 22 is equal to 8.

Moreover, the color marks 22 in a row 28 are longitudinally shifted by a second shift S2 with respect to corresponding color marks 22 in the circumferentially subsequent row 30.

Moreover, the color marks 22*c*, 22*d* of the row 30 are longitudinally shifted by a second shift S2 with respect to corresponding color marks 22*a*, 22*b* in the circumferentially subsequent row 28.

The second shift S2, similarly to the first shift S1, is defined by a number of subsequent and adjacent exposed portions of yarns along the longitudinal direction L of the suture 10. The second shift S2 is in particular determined by counting the adjacent exposed portions of yarns while moving, along the longitudinal direction L, from the beginning of a color mark 22 in a row (for example, the color mark 22*d* in row 30 in FIG. 1) to a longitudinal position corresponding to that of the beginning of a color mark 22 in a circumferentially subsequent row (for example, the color mark 22*b* in row 28 in FIG. 1).

The second shift S2 is constant and depends on the braiding configuration adopted. In the case shown in FIG. 1, in which a two over/two under braiding configuration is adopted, the second shift is equal to 2.

In particular, the value of the second shift S2 is related to the value of the first shift S1 according to the above formula (4).

For example, in the case of FIG. 1, in which the first shift S1 is equal to 8 and X is equal to ¼ (see formula (2) above), the second shift is equal to 2.

All the color marks 22 of the suture 10 form a regular pattern along the outer surface of the outer sheath 12, and they are in particular arranged along a number of ideal helixes running onto an external surface of the outer sheath 12 and all having a constant pitch that is equal to the first shift S1.

As detailed above, the suture 10 is formed by braiding the background yarns 14 and the at least two colored yarns 16, 18 of the outer sheath 12 on a known braiding machine.

Figure 2:
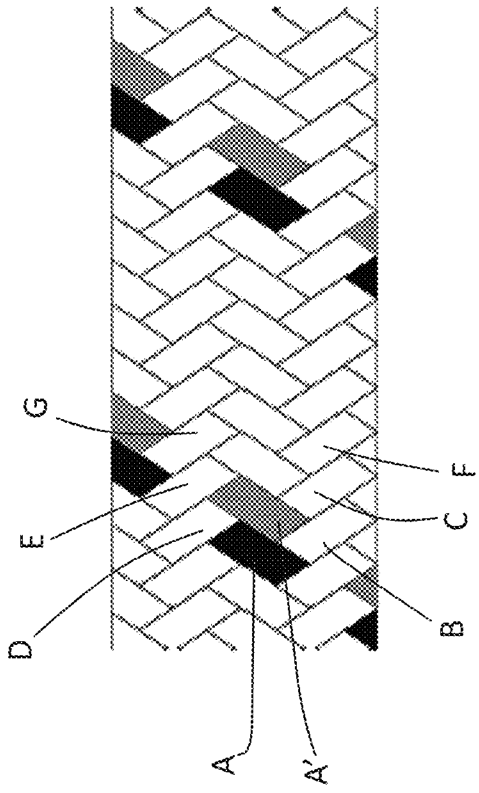
FIG. 2 is a schematic representation of a braiding configuration of a suture according to embodiments of the invention.

The braiding machine is set so as to produce, in the outer sheath 12 of the suture 10, a “two over/two under” braiding configuration, which is schematically represented in FIG. 2. According to this configuration, each yarn alternately overlays two yarns before being superimposed by the following two yarns.

In particular, the two over/two under configuration provides that if one follows the path of a first reference yarn A (that might be, by way of example, the first yarn 16 of FIG. 1), it can be recognized that it is alternately overlaying two yarns B, C before being superimposed by the following two yarns D, E. Similarly, a second reference yarn A' (that might be, by way of example, the second yarn 18 of FIG. 1) that is adjacent to the first reference yarn A is alternately overlaying two yarns C, F before being superimposed by the following two yarns E, G.

The regular arrangement of the color marks 22 of FIG. 1 along an ideal helix, outlined above, is in particular produced according to the setting of the braiding machine used and to the resulting braiding configuration shown in FIG. 2.

According to this configuration, an absolute value of the braiding angle of braided yarns of the suture 10 is comprised between 20° and 60°.

Figure 3:
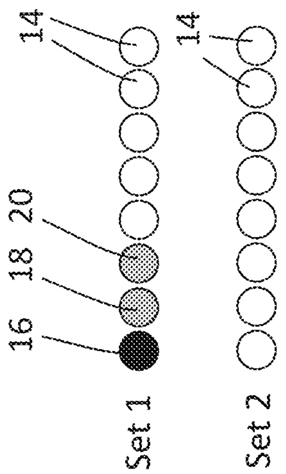
FIG. 3-4 are schematic representations of the two sets of bobbin carriers of a maypole braiding machine set for braiding sutures having two different color marks according to the invention.
Figure 4:
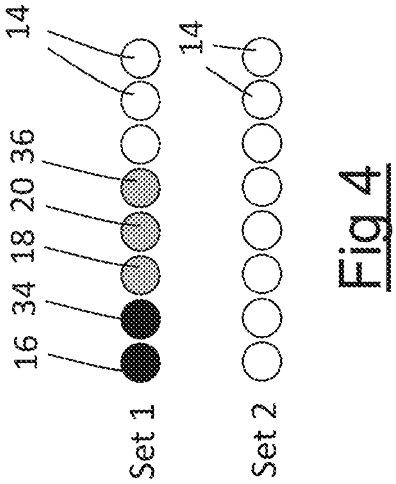

FIG. 3-4 schematically illustrate two possible distributions of the various yarns onto bobbins of the first set (Set 1) and of the second set (Set 2) of the braiding machine used, in order to manufacture sutures having two color marks according to different embodiments of the invention.

In FIG. 3-4, bobbin carriers of each set are shown in a line only to highlight the sequence of yarns loaded onto the bobbins of each set, but their actual spatial arrangement onto the braiding machine is substantially circular.

In both FIG. 3-4, Set 1 can be for example constituted by bobbin carriers rotating clockwise during the braiding operation, and Set 2 can be for example constituted by the bobbin carriers rotating counterclockwise during the braiding operation, but they might be inverted.

In the configuration of FIG. 3, adjacent bobbin carriers of Set 1 carry in a sequence first, second and third yarns 16, 18, 20 having a respective first, second and third color, and the remaining bobbin carriers of Set 1 carry background yarns 14, as well as all the bobbin carriers of Set 2.

The background color of the background yarns 14, the first color of the first yarn 16, and the second color of the second yarn 18, all different from one another, are respectively represented again by white, black and grey. The third color of the third yarn 20 is the same as the second color and is thus also represented as grey.

The sequence of first, second and third yarns 16, 18, 20 as loaded onto the bobbin carriers of Set 1 corresponds to the actual sequence (and corresponding "color code") exposed by the color marks 22 obtained by braiding the suture 10 onto the braiding machine.

In particular, this configuration of the sets of bobbin carriers results in the color marks 22 of the suture 10 showed in FIG. 1.

As stated above, the suture 10 can comprise further colored yarns.

In the embodiment of FIG. 4, the suture 10 comprises a total of five colored yarns. Adjacent bobbin carriers of Set 1 carry the first, the second and the third yarns 16, 18, 20 and in addition a fourth and a fifth yarn 34, 36. The remaining bobbin carriers of Set 1 carry background yarns 14, as well as all the bobbin carriers of Set 2. The background yarns again have the same background color, represented as white.

The first and the fourth yarn 16, 34 have the same first color, represented as black, whereas the second, third and fifth yarns 18, 20 and 36 have the same second color, represented as grey, both differing from one another and from the background color. As shown, yarns having a same color are placed on adjacent bobbins and therefore, based on the colors outlined above, the eight bobbins of Set 1 carry in a sequence the first yarn 16, the fourth yarn 34, the second yarn 18, the third yarn 20 and the fifth yarn 36. This sequence corresponds to the "color code" exposed by the color marks resulting by braiding the suture onto the maypole braiding machine.

The color marks resulting from the bobbin configurations of FIGS. 3 and 4, advantageously present two distinct adjacent colored regions, each constituted by adjacent exposed portions of colored yarns having a same color, thereby being particularly easy to identify.

In embodiments not shown, further colored yarns up to a total of seven colored yarns can be added to increase the length of the color marks, provided that such pattern is and defines a directional that allows to discern opposite ends of the suture.

Similarly to FIGS. 3 and 4, in these embodiments the colored yarns are preferably either of the first or of the second color, and colored yarns of a same color are adjacent to each other, so that in the color patterns two distinct adjacent colored regions constituted by adjacent exposed portions of colored yarns of a same color.

By way of a non-limiting example, in actual sutures the background color can be white, the first color can be black, the second color can be blue, and the third color can be yellow.

Although suture threads have been exemplarily illustrated and described with particular reference to FIG. 1, the invention applies, mutatis mutandis, also to different types of suture such as flat sutures (e.g. suture tapes).

The invention claimed is:

1. A suture having an outer sheath comprising a plurality of color marks and a background visually distinguishable from the color marks, wherein said plurality of color marks are arranged in at least one row along a longitudinal direction of the suture, each color mark being longitudinally shifted with respect to a subsequent color mark in a same row by a first shift, wherein each color mark comprises more than two exposed portions of colored yarns in the same row along the longitudinal direction of the suture, wherein each color mark does not comprise exposed portions of said background in the same row along the longitudinal direction of the suture, wherein at least two colored yarns respectively have a first color and a second color, wherein at least a further colored yarn has a respective color selected from: said first color, said second color and at least one other color different from said first color and said second color, wherein each color mark comprises at least exposed portions of said first color and of said second color, wherein, in each color mark, exposed portions of colored yarns of a same color are adjacent to one another along the longitudinal direction of the suture, wherein said background comprises exposed portions of background yarns of a background color, said background yarns and said colored yarns being braided to each other, said first color and said second color being different from said background color and said first color being different from said second color, wherein the exposed portions of the colored yarns of each color mark are substantially parallel to each other and arranged in a sequence along the longitudinal direction of the suture, and wherein the sequence of more than two exposed portions of colored yarns is repeated in the same row along the longitudinal direction of the suture.

2. The suture according to claim 1, wherein said at least one row along the longitudinal direction of the suture comprises a plurality of rows circumferentially spaced from adjacent ones by at least one background row, said at least one background row comprising only exposed portions of background yarns.

3. The suture according to claim 2, wherein said plurality of rows comprises at least two rows circumferentially spaced apart from adjacent ones.

4. The suture according to claim 3, wherein said plurality of rows comprises four rows circumferentially spaced apart from adjacent ones by 90°.

5. The suture according to claim 2, wherein each color mark is longitudinally shifted with respect to a subsequent color mark in a same row of any row by said first shift.

6. The suture according to claim 5, wherein any color mark of a first row is longitudinally shifted by a second shift along the longitudinal direction with respect to a corresponding color mark in a second row circumferentially subsequent to the first row.

7. The suture according to claim 6, wherein said second shift is defined by a number of subsequent and adjacent exposed portions of yarns along a longitudinal direction, and is equal to X*S1, wherein S1 is the first shift, and X is calculated according to the formula:

$$X=4/b$$

with b being an even number.

8. The suture according to claim 5, wherein all the color marks of the suture are arranged along a number of helixes running onto an external surface of the outer sheath and all having a constant pitch.

9. The suture according to claim 1, wherein said first shift is defined by a number of subsequent and adjacent exposed portions of yarns along a longitudinal direction, wherein said number of subsequent and adjacent exposed portions of yarns is equal to half of the total number of braided yarns of the suture.

10. The suture according to claim 1, wherein each color mark comprises less than 13 exposed portions of colored yarns.

11. The suture according to claim 1, wherein each colored yarn is either of the first color or of the second color.

12. The suture according to claim 1, wherein said outer sheath has a two over/two under braiding configuration.

13. The suture according to claim 1, wherein a raw material of all the yarns constituting the outer sheath of the suture is Ultra-High Molecular-Weight Polyethylene (UHMWPE).

* * * * *